United States Patent
Sari-Sarraf et al.

(10) Patent No.: US 6,553,133 B1
(45) Date of Patent: Apr. 22, 2003

(54) FOUR-DIMENSIONAL CHARACTERIZATION OF A SHEET-FORMING WEB

(75) Inventors: Hamed Sari-Sarraf, Lubbock, TX (US); James S. Goddard, Clinton, TN (US)

(73) Assignee: U.T. Battelle, LLC, Oak Ridge, TN (US)

(*) Notice: Subject to any disclaimer, the term of this patent is extended or adjusted under 35 U.S.C. 154(b) by 0 days.

(21) Appl. No.: 09/401,102

(22) Filed: Sep. 22, 1999

(51) Int. Cl.[7] .................................. G06K 9/00
(52) U.S. Cl. ........................ 382/112; 356/429
(58) Field of Search ........................ 382/112, 149; 359/254, 320, 258, 322, 245; 478/131, 218; 356/402, 237.1, 430, 127, 243.5, 429

(56) References Cited

U.S. PATENT DOCUMENTS

| | | | |
|---|---|---|---|
| 4,947,684 A | 8/1990 | Balakrishnan | 73/159 |
| 4,950,911 A | 8/1990 | Williams et al. | 250/563 |
| 5,560,979 A * | 10/1996 | Bloom et al. | 428/195 |
| 5,563,809 A * | 10/1996 | Williams et al. | 364/560 |
| 6,072,551 A * | 6/2000 | Jannson et al. | 349/64 |

* cited by examiner

*Primary Examiner*—Jayanti K. Patel
*Assistant Examiner*—Seyed Azarian
(74) *Attorney, Agent, or Firm*—Andrew Y. Pang; Nexsen Pruet Jacobs & Pollard, LLC (57) ABSTRACT

A method and apparatus are provided by which a sheet-forming web may be characterized in four dimensions. Light images of the web are recorded at a point adjacent the initial stage of the web, for example, near the headbox in a paperforming operation. The images are digitized, and the resulting data is processed by novel algorithms to provide a four-dimensional measurement of the web. The measurements include two-dimensional spatial information, the intensity profile of the web, and the depth profile of the web. These measurements can be used to characterize the web, predict its properties and monitor production events, and to analyze and quantify headbox flow dynamics.

11 Claims, 11 Drawing Sheets

| $\|\nabla F\|$ | $\lambda_1$ | $\lambda_2$ | $\nabla F \cdot E_1$ | $\nabla F \cdot E_2$ | LABEL |
|---|---|---|---|---|---|
| 0 | 0 | 0 | 0 | 0 | FLAT |
| 0 | − | − | 0 | 0 | PEAK |
| 0 | + | + | 0 | 0 | PIT |
| 0 | − | 0 | 0 | 0 | RIDGE |
| 0 | + | 0 | 0 | 0 | RAVINE |
| 0 | − | + | 0 | 0 | SADDLE |
| 0 | + | − | 0 | 0 | SADDLE |
| + | 0 | 0 | * | * | SLOPE |
| + | − | * | 0 | * | RIDGE |
| + | * | − | * | 0 | RIDGE |
| + | + | * | 0 | * | RAVINE |
| + | * | + | * | 0 | RAVINE |
| + | − | − | −,+ | −,+ | HILLSIDE (CONCAVE) |
| + | − | 0 | −,+ | * | HILLSIDE (CONCAVE) |
| + | − | + | −,+ | −,+ | HILLSIDE (SADDLE) |
| + | + | − | −,+ | −,+ | HILLSIDE (SADDLE) |
| + | + | 0 | −,+ | * | HILLSIDE (CONVEX) |
| + | + | + | −,+ | −,+ | HILLSIDE (CONVEX) |

FOUR-DIMENSIONAL CHARACTERIZATION OF A SHEET-FORMING WEB

STATEMENT OF GOVERNMENT RIGHTS

This invention was made with United States Government support under Contract Number DE-AC05-96OR22464 awarded by the United States Department of Energy to Lockheed Martin Energy Research Corporation and the United States Government has certain rights in this invention.

FIELD OF THE INVENTION

This invention relates to methods and apparatus for characterizing and monitoring a web BN in a sheet forming process such as paper making. More particularly, this invention relates to methods and apparatus for forming an image of a web at an initial point (the wet end) and applying image analysis and pattern recognition techniques to the image to produce measurements of two-dimensional spatial information and the intensity and depth profiles of the web.

BACKGROUND OF THE INVENTION

Many production processes involve the use of sheet-forming apparatus, including the making of paper, thin plastic films, certain types of float glass, and some metal sheet processes. Whether formed by the flow of a slurry onto a fourdrinier apparatus as in paper-making or extruded from a die head as in the production of plastic films, there is an initial formation of a web. The web may be further processed. In paper-making, for example, the web is dried and calendared and may be coated before being taken onto a take-up reel for transportation or storage. In the production of plastic films, on the other hand, the only further processing needed may be the curing of the plastic resin.

Different types of sensors and different types of systems have been developed to measure properties of paper and of the paper web. Some of these systems operate on-line, that is, during the paper-making process. Others are used for off-line analysis, as for quality control or research.

A large majority of these systems are intended for use at the dry end of the web-forming process. While such systems may be useful for some quality control purposes and characterization, the analysis is made after the web has been processed to at least some extent, i.e., in paper-making the web has been dried and calendared and in plastics the web has at least started to cure. Thus, some characteristics unique to the wet end have been altered or lost by the time the system has assessed the web.

Even in systems providing for observation of the wet end, observation of the dry end is either required or recommended. U.S. Pat. No. 5,563,809, issued Oct. 08, 1996 (Williams et al.) assigned to ABB Industrial Systems, Inc., proposes a stationary scanner near the wet or initial end of a web. The stationary detector scans across the web in the cross direction (CD) while the web moves in the machine direction (MD). The result is a raster scan of the web. The detected points are digitized and processed by a look up table and a reference memory. For control of the web manufacturing machine, however, a second detector located near the dry end of the web is needed.

Other systems that provide for detection of a web near the wet or initial end also use a scanning methodology. Due to the use of stationary detectors and the movement of the web, most such scanners scan in a raster pattern. Such scanning results in analyzing and/or detecting much less than 100% of the web.

There is thus a need in the art for methods and apparatus that can provide highly detailed and complete information by which a web can be characterized and by which other goals, such as improved headbox and die flows, can be accomplished.

SUMMARY OF THE INVENTION

It is an object of this invention to provide a method and apparatus for characterizing a web in a sheet forming process.

It is also an object of this invention to provide a method and apparatus for making and processing an image of a portion of a web to provide spatial, homogeneity, and intensity characteristics of the web.

It is likewise an object of this invention to provide a method and apparatus for characterizing a web with respect to the depth profile thereof.

It is further an object of this invention to provide a method and apparatus whereby a portion of a web can be imaged to allow processing of the image to provide data regarding spatial information in both the cross direction and machine direction of the web, the homogeneity and intensity thereof, and the topography thereof.

It is moreover an object of this invention to provide a method and apparatus that can provide the foregoing information in real time.

It is another object of this invention to provide one subsystem capable of characterizing a web with respect to homogeneity and intensity data and a second subsystem capable of providing a depth profile of the web at the same point, and to provide a method for correlating these characteristics to enable four-dimensional characterization of the web.

It is also an object of this invention to provide information characterizing a web from which the dynamics of the web-forming material, and the characteristics of the headbox or die can be studied, monitored, and controlled.

These and other objects are provided by a method of forming an image of a web of sheet-forming material near an initial point, digitizing said image to form a digital representation of said image, processing said digital representation to provide output signals representative of the spatial characteristics of said web in a cross direction and machine direction, the intensity profile of said web, and the depth profile of said web.

These and other objects are also achieved by providing apparatus having at least one stroboscopic source of light energy for stroboscopically illuminating a web of sheet-forming material, recording means for recording an image of said web during said illumination, digitizing means for digitizing said image to provide a digital representation thereof, processing means for processing said digital representation using image processing and pattern recognition algorithms, and an output means for providing signals representative of spatial information in the machine and cross directions of the web, the intensity profile of the web, and the, depth profile of the web.

BRIEF DESCRIPTION OF THE DRAWINGS

FIGS. 3(a)–3(f) are an illustration of the application of the multiscale wavelet representation transform and roughness analyses according to the invention, where FIGS. 3(a), 3(c), and 3(e) are applied to a nominal web surface and FIGS. 3(b), 3(d), and 3(f) are applied to a web surface with a streak.

FIGS. 9(a)–9(d) illustrate the topographic analysis according to the invention, where FIGS. 9(a) and 9(b) are of a paper slurry and FIGS. 9(c) and 9(d) are of water.

DETAILED DESCRIPTION OF THE INVENTION

The current invention provides a unique method and apparatus for producing an image of a web of sheet-forming material, and processing the image in real-time. Using novel image processing and pattern recognition algorithms provides spatial information and intensity and topographic information for the image. The invention also provides a unique method and apparatus for using a structured light source and processing algorithms to produce a depth profile of the web. These submethods and subsystems can be correlated on-line and in real time to produce four-dimensional information regarding the web. The produced data can be used to control the quality of the finished product, and can provide novel and useful tools for analyzing the operation of the headbox or die from which the sheet-forming material flows. These tools can be used in manufacturing operations and in research operations.

The methods and apparatus of the current invention are not limited to any particular sheet-forming material. Processes for forming sheets of material include paper making, plastic film production, glass production (particularly float glass production), and metal sheet production. The description herein focuses on the method and apparatus as adapted to a paper-making process. The invention can easily be adapted for use with other types of materials.

In brief, the invention is a method and apparatus for using a vision sensor to inspect and characterize the paper web at the wet end of a paper machine. By wet end is meant the region between the head box and the dryline. The characterization includes measurement of spatial information in the machine direction (MD) and in the cross direction (CD), the intensity profile at each coordinate, and the depth profile at each coordinate. Image analysis and pattern recognition algorithms are applied to these measured quantities to derive a four-dimensional characterization of the wet-end web.

The paper industry, and others using processes for producing webs, have had a long-standing need to better understand and robustly control the upstream process, specifically in the forming, or wet-end, section. The current invention comprehends a vision-based system that automatically measures and interprets the pertinent web parameters at the wet end.

Currently available sensing systems are intended to operate downstream. Unlike these, this invention provides the capability of generating timely, that is, real time, measurements of the important web parameters at the crucial stage of paper formation. Having this capability will dramatically impact product quality and production yield. In the short term, the ability to characterize the web at the wet end will provide the machine operators with the necessary feedback they need to make adjustments to the headbox (or forming die) and minimize the undesirable effects of formation variations. In the long term, better understanding and quantification of the headbox flow dynamics will allow researchers to make significant advances in headbox design and control.

The wet-end characterization of the web by this invention involves a four-dimensional (4-D) measurement of the slurry (fiber and water mixture, in the case of papermaking) in real time. The measurements include the two-dimensional (2-D) spatial information in the x (MD) and y (CD) coordinates, the intensity profile $f(x,y)$, and the depth profile $z(x,y)$ of the slurry. To infer the pertinent web parameters from these measurements, the method and apparatus employ a suite of sophisticated image processing and pattern recognition algorithms. Automatically inferred parameters, such as the homogeneity of the web, and location and topography of the web streaks, will then be used to quantify paper formation characteristics or to monitor production events, such as table activity and web breaks. The system will track these web features in the machine direction from the headbox to the dryline.

The data that will comprise the 4-D characterization are obtained via two subsystems. The first subsystem, the stroboscopic subsystem, acquires intensity images of the web using a CCD (charge-coupled device) camera and a strobe light to freeze motion. The second subsystem is the depth-profiling subsytem whereby the depth profile of the web is measured in real time using a CCD camera and structured lighting. The same or multiple cameras may be used for both the intensity image acquisition and the depth profile measurement. When the same camera is used, a subset of the image frames from the camera is used to acquire intensity images while the remaining frames are used for depth measurement. Depth measurement is accomplished by illuminating the web with a specific light pattern, such as lines or points, using either coherent light from a laser or incoherent light produced by a projector. The camera is offset from the light by an angle with respect to the surface of the web. The two subsystems may comprise separate apparatus, with the data from each being collated and combined to produce the 4-D characterization, or the two subsystems may be integrated into a single system.

The first of the two subsystems forming part of this invention is for stroboscopic image acquisition and data processing. The basic apparatus elements of this system include a high-intensity stroboscopic light source, an image recorder such as a charge-coupled device (CCD) camera, and processing support in the form of data storage means and computer support having the appropriate image acquisition and processing hardware and software.

A stroboscopic light source is used to illuminate the web near the initial point, that is, for paper-making, at a point just downstream of the headbox. The light source is preferably of high enough intensity to help eliminate the effects of ambient light. The recording device, preferably in the form of a CCD camera, is positioned to capture the image of the web as illuminated by the stroboscope. Exposure control of the CCD camera, combined with the high intensity of the light source, reduces the effect of ambient light. Additional equipment, such as polarizing filters and other filters, can be added to improve the quality of the image captured.

The CCD camera is connected to a data storage means which includes a digitizer providing a digital representation of the image collected. The representation is stored and can be retrieved in real time for image processing and to provide feedback to the operator of the web equipment. The storage also provides a record that can be analyzed off-line for planning and research purposes. The data storage means includes or is connected to a processing unit for performing the image processing described below.

The light source, CCD camera, and data storage means can be used to capture images on almost any desired time scale. That is, discrete segments of the web can be imaged and analyzed to perform periodic checks on the web. Alternatively, in a preferred mode of the invention, the equipment is used to provide images which comprehend 100% of the web. This provides real-time monitoring of the entire web production. The light source and camera can be clocked so as to capture sequential images, or a desired percentage of overlap of images can be achieved.

Figure 1:
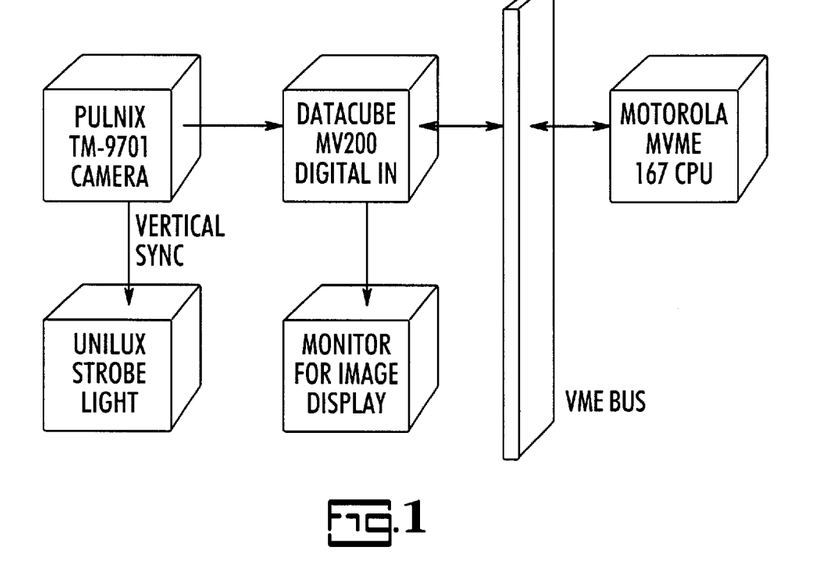
FIG. 1 is a block diagram of an exemplary stroboscopic subsystem according to the invention.

Having described the stroboscopic system in general, the following apparatus is provided for exemplary but not limiting purposes. The imaging equipment included a Pulnix TM-9701 CCD camera; a Schneider 25-mm focal length C-mount lens; a Tiffen screw-on mount circular polarizing filter; a Unilux Hi-Lighter Strobe Light, Model HI-RR-6.0-VC. The data storage and processing equipment included a Datacube Maxvideo MV200 and a Motorola MVME167 image acquisition and processing system. A block diagram of the subsystem as described is shown in FIG. 1.

This particular CCD camera is a progressive scan device with 768 horizontal pixels and 484 vertical pixels. The camera produces images at 30 frames per second with manually selectable electronic exposure control. Exposure control was necessary in the test set-up even with the strobe because ambient light can cause a significant background signal with large variations over the image. This variation was observed when the integration time was equal to the frame acquisition time of 33 ms. Reducing the exposure time to 500 $\mu$s eliminated the interference even at the high ambient light levels present in a working paper mill.

The Unilux light is rugged enough to withstand the harsh environments of high temperatures and humidities that exist in working mills. The named model uses a Xenon flash tube with a flash rate of about 6,000 flashes per minute with a maximum energy of about 4.7 joules per flash. Flash duration is about 20 $\mu$s. A remote control unit allows manual control of intensity, flash rate, and phase. To acquire images at the time the strobe flashes, the light includes a video input used to synchronize the strobe to the camera. The strobe triggers on the vertical sync signal from the camera so that the relative time between the strobe flash and the CCD readout is fixed. The manual phase control is used to adjust the time delay between the sync signal and the strobe firing so that the integration time window for the camera of 500 $\mu$s falls within the strobe flash.

In the processing units, the Datacube is used for real-time acquisition and storage of the camera images. This capacity of this unit is limited to about 160 frames, which is less than 5 seconds of image data. Addition of a Datacube MD1 disk array with a recording capability of about 8 gigabytes increased this time to about 12 minutes. A backup tape drive can be used to back up the memory, permitting reuse of the active memory.

In tests, the camera field of view was about 4 feet wide. At this width, pixel resolution is about 0.06 inches. A web moving at a typical rate of about 1500 ft/min will move about 0.006 inches during the strobe time of 20 $\mu$s. This is a ratio of about 10 to 1 for resolution to motion distance, which results in negligible blur. Test results show that a thin ink line drawn in the cross direction on a test web moving at about 1000 ft/min gave a sharp image of only about 2 to 3 pixels wide, with no blurring evident.

The image data collected in the data storage means is processed by means of novel algorithms to extracted pertinent features of the web. A preferred characterization of the web is based on the apparent homogeneity of the images, and hence of the web. This characterization is related to the web forming properties of the web apparatus. It also relates to the formation index, which is most widely measured, currently, off-line with the aid of a densitometer.

The image processing performed by the apparatus of the invention, and forming a step of the method of the invention, detects and characterizes unique formations in the web, for example, streaks. The image processing includes two techniques that are combined to measure the apparent homogeneity of the texture images of the web captured by use of the strobe light and the camera. The techniques are wavelet transformation and derivation of the correlation dimension.

The first step in measuring the homogeneity of the captured images, and hence of the web itself, is subjecting the digital representation data to a discrete wavelet transform algorithm. While there are many forms of wavelet transforms, the preferred class of two-dimensional wavelet transform used herein is the multiscale wavelet representation transform(MSWAR). The primary difference between MSWAR and standard discrete wavelet transform is that the generated signals or images in MSWAR remain at full resolution. In standard discrete wavelet transform, resolution is reduced through decimation with each iteration of the transformation process. To achieve the high object recognition and feature extraction that is an achieved goal of the current invention, the retention of resolution possible with MSWAR affords more data points and hence more accurate analysis.

The function of the MSWAR transform is to enhance the edges of features within the image. By extracting these discontinuities between one area of the image and another, measurements can be obtained of the homogeneity of the overall image.

The MSWAR of a 2-D discrete signal (image) F(x,y), where (x,y)=1, 2, . . . , N, with M levels of scale reduction is a set of (3M+1) signals. The details signals at all levels of scale reduction are:

| | |
|---|---|
| $f^j_{d1}(x,y)$ | (no vertical edges) |
| $f^j_{d2}(x,y)$ | (no horizontal edges) |
| $f^j_{d3}(x,y)$ | (no horizontal or vertical edges) | for j=1, 2, . . . , M, plus the blurred version f(x,y) at the lowest scale level $f^M(x,y)$. An efficient algorithm for the generation of these images is:
1. Given a low-pass and a high-pass filter, and assuming that these filters are represented as column vectors LP and HP, respectively, generate four 2-D kernels as follows:

LP(LP)$^t$, HP(LP)$^t$, LP(HP)$^t$, HP(HP)$^t$, where (.)$^t$ is vector transposition.
2. For j=1, 2, ..., M
3. For x=0, 1, ..., N-1
4. For y=0, 1, ..., N-1
5. Allocate u row pointers $p_0, p_1, \ldots, p_{u-1}$ and u column pointers $q_0, q_1, \ldots, q_{u-1}$, where u indicates the support of the selected filters
6. Initialize the pointers as follows:
   $p_0=x, p_1=p_0+2^{j-1}, \ldots, p_{u-1}=p_{u-2}+2^{j-1}$
   $q_0=y, q_1=q_0+2^{j-1}, \ldots, q_{u-1}=q_{u-2}+2^{j-1}$
7. Convolve the generated kernels with the elements of the signal $f^{j-1}$, where $f^0=f(x,y)$, as addressed by the above pointers. The results are the $(x,y)^{th}$ elements of the four output signals $f^j$, $f^j_{d1}$, $f^j_{d2}$, and $f^j_{d3}$, respectively.
8. Next y.
9. Next x.
10. Next j.

The choice of low-pass and high-pass filters is application-dependent. Daubechies' filters (I. Daubechies, "Orthogonal Bases of Compactly Supported Wavelets," *Comm. Pure and Appl. Math* 41, pp. 909–996, 1988) provide compact support and orthogonality, for example.

Figure 2A:
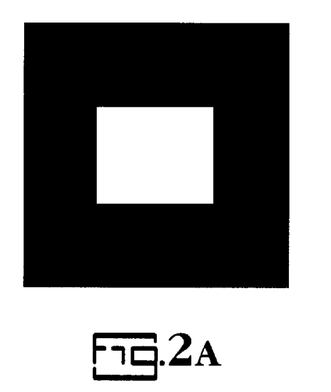
FIGS. 2(a) and 2(b) are an illustration of the application of the multiscale wavelet representation transform according to the invention, applied to an arbitrary image.
Figure 2B:
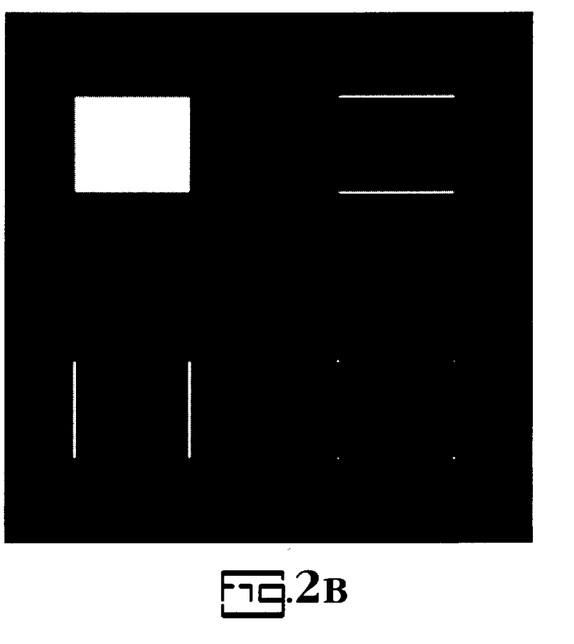

FIG. 2 shows that application of the foregoing algorithm. FIG. 2(a) is an arbitrary image to which the algorithm is applied. FIG. 2(b) shows the MSWAR of this image. The upper left representation in FIG. 2(b) is $f^j$; the upper right is $f^j_{d1}$ (no vertical edges); the lower left is $f^j_{d2}$ (no horizontal edges; and the lower right is $f^j_{j3}$ (no horizontal or vertical edges—the image should appropriately reflect only the four points of the corners of FIG. 2(a), which are neither horizontal nor vertical). The images show the automatic decomposition of the high-frequency components (the edges) of the input image into horizontal and vertical images. The wavelet transform and the MSWAR, because of the multiscale nature, allow a choice of the appropriate scale of operation, that is, a specific level of scale where the desired image features are accentuated or attenuated and/or the image clutter is attenuated.

The scale to be selected for the above processing is based on factors such as the expected roughness of the web surface and the size of structures therein expected to be encountered. The actual scale required to adequately characterize a given web or type of web can first be estimated. Preliminary imaging and measuring will then provide additional data from which the desired scale can be determined such that the feature size discrimination is appropriate to the particular application.

The second step in the imaging processing is measurement of the correlation dimension from digital images. This requires processing the image data to quantify the surface characteristics of the images, utilizing the MSWAR transforms obtained. The correlation dimension, a fractal-based measurement, is utilized for this purpose. In the current invention, two new measurements, derived from the correlation dimension, are used. The first of these provides quantification of the surface roughness, and the second provides a measure of the surface homogeneity in a global sense.

The correlation dimension is derived as follows. A grey level image f(x,y) can be represented by a point in three dimensional space as $\vec{X}_i[x,y,f(x,y)]$, i=1, 2, ..., N. The correlation dimension, from P. Grassberger and I. Procaccia, "Characterization of Strange Attractors," *Phys. Rev. Letters* 50, No. 5, pp. 346–349, 1983, is defined as $$v = \lim \{\log[C(\epsilon)]/\log[\epsilon]\}$$

where the limit is taken $\epsilon \to 0$, and $\epsilon$ denotes scale. The correlation sum $C(\epsilon)$ is given as $$C(\epsilon) = \lim N^{-2} \Sigma \theta(\epsilon - \|\vec{X}_i - \vec{X}_j\|)$$

where the limit is taken $N \to \infty$ and the summation is i,j=1 to N ($i \neq j$); N is the total number of points in the set; $\theta(x)$ denotes the unit step function, and $\|\vec{X}_i - \vec{X}_j\|$ is the distance between vectors $\vec{X}_i$ and $\vec{X}_j$. Generally, the correlation dimension is estimated as the slope of the line that is fitted to the data points $\{\log[\epsilon], \log[C(\epsilon)]\}$. For the current invention, however, two new measurements are derived directly from the correlation sum.

The first measurement derived from the correlation sum according to the invention reflects the total roughness of the input image surface. This measurement is R (m,n) where $$R(m,n) = \Sigma C^2(\epsilon, m, n)$$

where the summation is $\epsilon=1$ to $\epsilon_u$, where $\epsilon_u$ is the upper limit for $\epsilon$, and $C(\epsilon, m, n)$ is the correlation sum computed within non-overlapping subregions of the input image. The second measurement quantifies global image homogeneity and is computed as:

$$V = Q^{-1} \Sigma_m \Sigma_n [R(m,n) - M]^2$$

where $$M = Q^{-1} \Sigma_m \Sigma_n R(m,n)$$

and Q is the total number of subregions into which the input image is divided. With these defined values, high values of R(m,n) signify high correlation among the pixel values in the subregion, corresponding to a smooth surface, and low values of R(m,n) indicate a rough surface, that is, low correlation among the pixel values. Small values of V denote a homogeneous region wherein the surface is either mainly rough or mainly smooth.

Figure 3A:
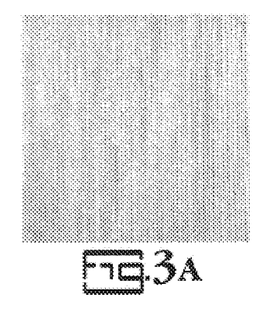
Figure 3B:
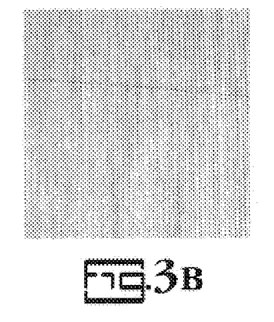
Figure 3C:
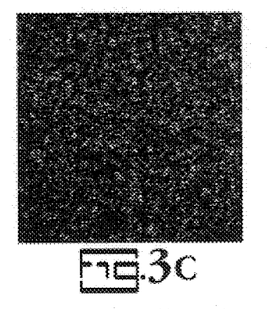
Figure 3D:
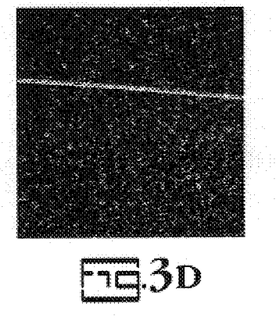
Figure 3E:
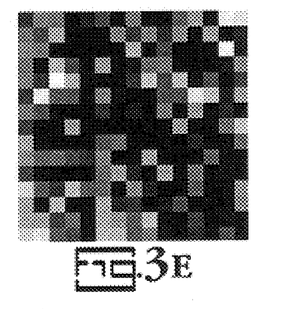
Figure 3F:
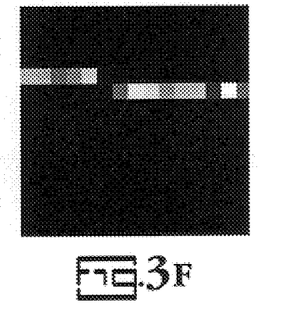

Combining MSWAR with the foregoing provides a tool for quantifying the surface characteristics of texture images. By applying the local roughness and global homogeneity measures to the output of MSWAR (specifically, the detail signals), these features can be quantified in a scale-dependent fashion. An application of this is illustrated in FIG. 3. FIGS. 3(a) shows a nominal surface, and (b) shows a surface with a streak. FIGS. 3(c) and (d) show, respectively, the $f^2_{d1}$ MSWAR image for (a) and (b). FIGS. 3(e) and (f), respectively, show the R(m,n) for the images in (c) and (d). The global homogeneity measure V for the input image (a) is 1.11, indicating relative homogeneity. The presence of the streak in (b), however, gives a V of 58.14 for (b), indicating a lack of homogeneity. Application of MSWAR effectively removes the natural texture of the input images (a) and (b) such that the streak in (b) has an accentuated impact on the homogeneity measurement.

A further algorithm provides an even more accurate detection and characterization of features in webs. This algorithm is used to provide characterization of the surface topography of the web. The algorithm is based on the facet model, aiding in characterization of topographic structures (such as streaks) visible in the intensity images of a slurry or web. Moreover, the algorithm is applied to the true three-dimensional (3-D) data gathered with the below-described second subsystem for depth profiling.

Figure 4A:
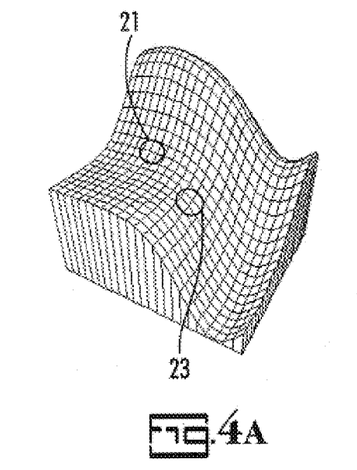
FIG. 4(a) and 4(b) show illustrative topographic structures that may be found on a web surface.
Figure 4B:
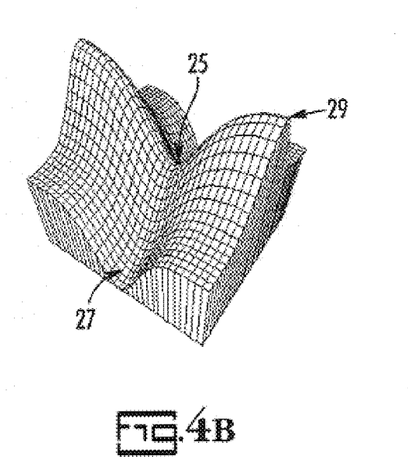

The facet model principle assumes that the intensity image can be characterized as a piecewise continuous gray level intensity surface. To carry out the characterization and processing with the observed digital image requires a model that describes the general form of the surface in the neighborhood of any pixel. The commonly used general forms for the facet model include piecewise constant, piecewise linear, piecewise quadratic, and piecewise cubic. With accurate images, not degraded by noise or geometrical transformations, the first step is to estimate the parameters of the underlying surface for all pixels and the respective neighborhoods thereof. The estimates are used to label each pixel into on of a variety of topographic structures such as peak, ridge valley saddle flat, and hillside. FIGS. 4(*a*) and 4(*b*) illustrate some of these structures, including a convex hillside 21 (FIG. 4(*a*)), a concave hillside 23 (FIG. 4(*a*)), a saddle point 25. (FIG. 4(*b*)), a ravine line 27 FIG. 4(*b*)), and a ridge line 29 (FIG. 4(*b*)).

For this invention, the least-squares best fit cubic facet is computed for each pixel and its neighborhood in the input image. The neighborhood can be chosen to be of any suitable size, depending on the resolution desired (or available) and the available computing power. In a neighborhood chosen to be 7×7, the cubic facets are cubic polynomials of the form:

$$F(x,y)=Ax+By+Cx^2+Dxy+Ey^2+Fx^3+Gx^2y+Hxy^2+Iy^3+J.$$

Figure 5:
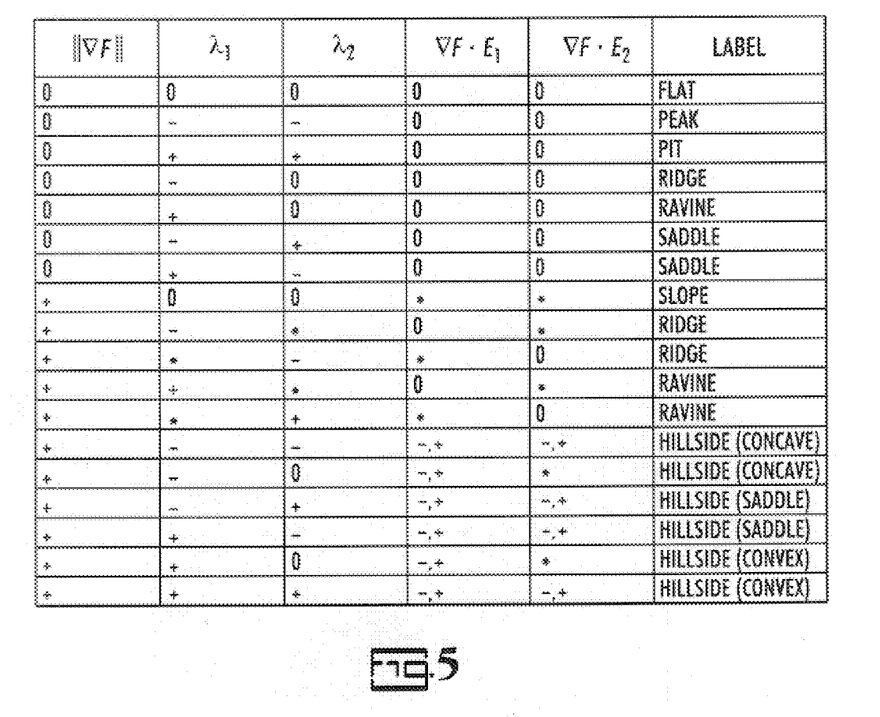
FIG. 5 is a table (Table I) showing the topographic features that may be defined and determined by application of part of the method of the invention.

Once the 10-element vector of coefficients has been estimated for each pixel, the topographic labeling proceeds by computing the gradient and the Hessian of the facets. These are defined as:

$$\begin{bmatrix} \frac{\partial F}{\partial x} \\ \frac{\partial F}{\partial v} \end{bmatrix} \text{ and } \begin{bmatrix} \frac{\partial^2 F}{\partial x^2} & \frac{\partial^2 F}{\partial x \partial y} \\ \frac{\partial^2 F}{\partial y \partial x} & \frac{\partial^2 F}{\partial y^2} \end{bmatrix},$$

respectively. It is then determined whether the various quantities are negative, zero, or positive. The values and respective labels are set forth in Table 1 in FIG. 5, wherein $\|\nabla F\|$ is the gradient magnitude $\lambda_1$ and $\lambda_2$ are the largest and the smallest eigenvalues of the Hessian, respectively $\nabla F \cdot E_1$ and $\nabla F \cdot E_2$ are the first directional derivatives in the direction of $E_1$ and $E_2$, which are the eigenvectors associated with $\lambda_1$ and $\lambda_2$, respectively, and "0" means close to zero; "+" means significantly different from zero on the positive side; "−" means significantly different from zero on the negative side; and "*" means it does not matter.

Figure 6A:
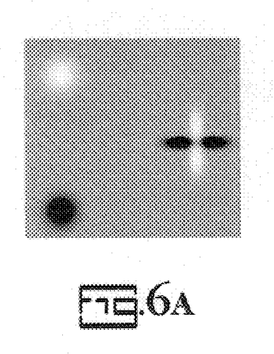
FIGS. 6(a)–6(c) illustrate the application of the topographic analysis of a test image according to the invention.
Figure 6B:
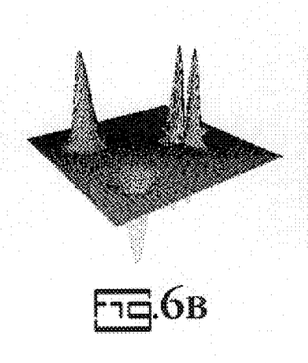
Figure 6C:
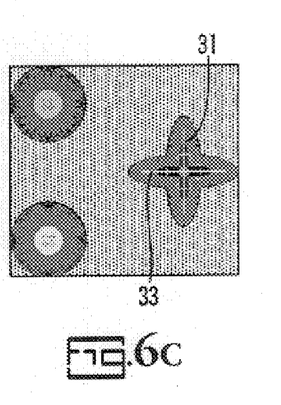
Figure 7A:
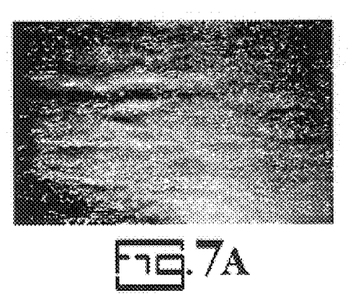
FIGS. 7(a)–7(g) illustrate images captured by apparatus according to the invention of a papermaking web for linerboard.
Figure 7B:
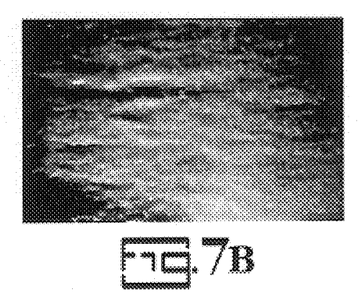
Figure 7C:
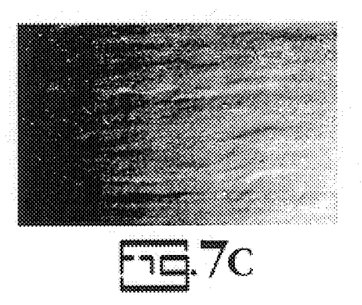
Figure 7D:
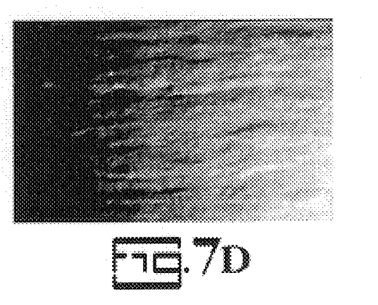
Figure 7E:
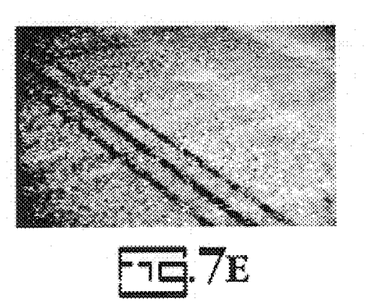
Figure 7F:
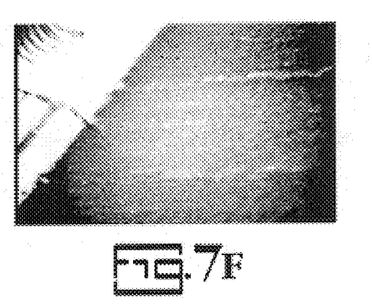
Figure 7G:
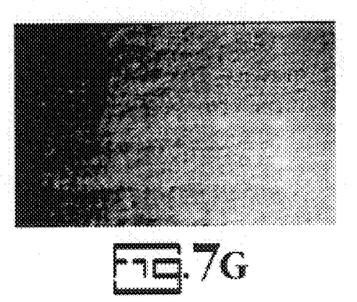
Figure 8A:
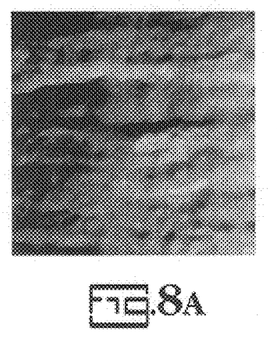
FIGS. 8(a)–8(d) contain illustrative images showing analysis of a linerboard web by the method according to the invention.
Figure 8B:
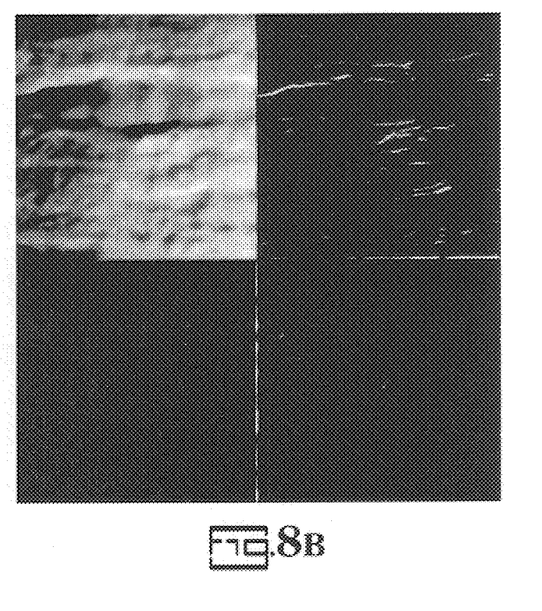
Figure 8C:
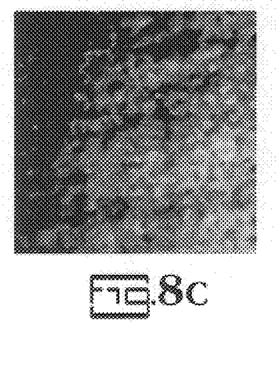
Figure 8D:
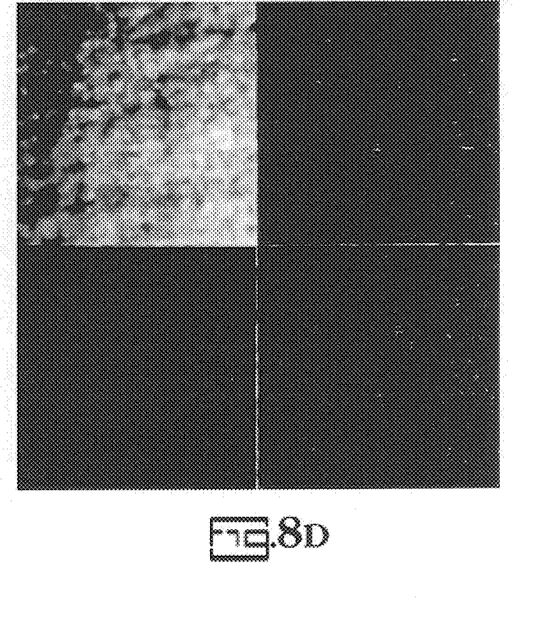
Figure 9A:
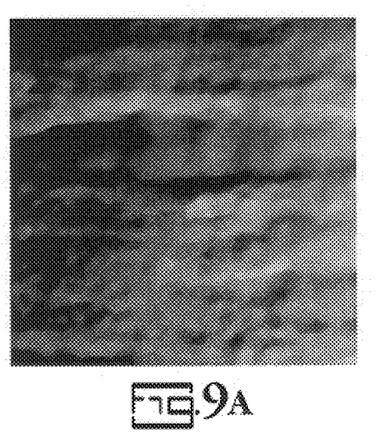
Figure 9B:
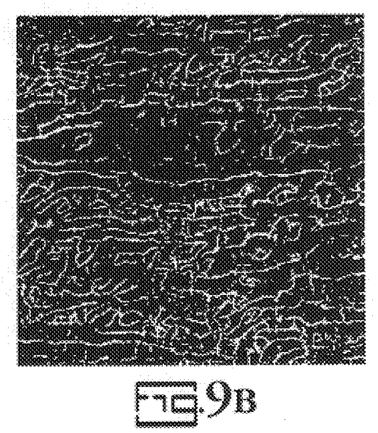
Figure 9C:
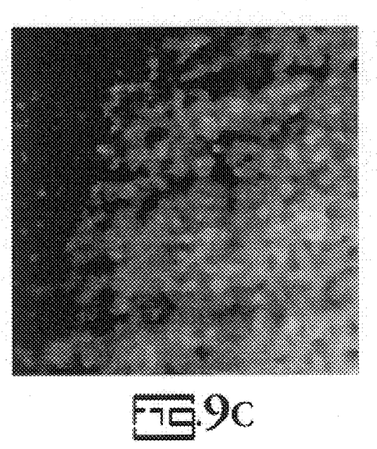
Figure 9D:
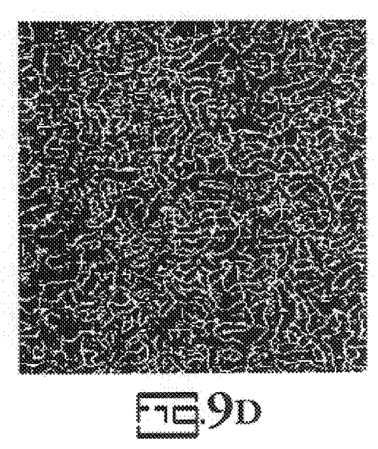

A synthetic image was tested via the algorithm, and the results are shown in FIG. 6. FIG. 6(*a*) shows the test image; FIG. 6(*b*) shows the derived intensity image in 3-D; and FIG. 6(*c*) shows the labeled topographic image, with a ridge line 31 and a ravine line 33 identified.

A test of this system was conducted on an operating machine producing linerboard. The line speed was about 1500 ft/min. The CCD camera was positioned about 4.0 ft above the web with a 3×4 ft. field of view. The center of the field of view was about 8 feet away from the headbox and about 2.5 feet away from the edge of the web. The resolution is about 0.063 inches per pixel. FIG. 7 shows sample images taken by the CCD camera. FIG. 7(*a*) shows a direct image, and illustrates a problem with specular reflection from water beads. Filtering the image by median filtering after acquisition (FIG. 7(*b*)) or by the use of polarizing filters effective before image acquisition (FIG. 7(*c*)) reduced this reflection. FIG. 7(*d*) shows the clarity of the image after median filtering. FIG. 7(*e*) also shows the clarity and sharpness of the images. FIG. 7(*f*) was taken to demonstrate the effect on the slurry of a small deposit (circled) on the lip of the headbox, creating web streaks. FIG. 7(*g*) is a comparison image of fiberless water, showing the distinction between a slurry and water.

The images were subjected to the image analysis algorithms described above. FIG. 8 illustrates the results. FIG. 8(*a*) is a subregion of an overhead shot of a slurry. FIG. 8(*b*) shows the four results of the MSWAR derivations, as described above with reference to FIG. 2. The analytical usefulness and accuracy of the method is demonstrated in that the detail image $F^j{}_{d1}(x,y)$ (upper right in FIG. 8(*b*)) detects non-uniformities in the machine direction as a result of the streak in the image FIG. 8(*a*), whereas the $f^j{}_{d2}$ image, in the cross direction, shows a more homogeneous web characteristic. The value V for the former is 751.3, indicative of nonhomogeneity, and the value V for the latter is 166.3, indicative of a higher degree of homogeneity for that image. This bears out the utility of the correlation measurements. As a comparison, FIG. 8(*c*) is an image of water only, and the transforms and the homogeneity measurements (V=38.9) clearly reflect the homogeneity of the image.

FIG. 9 shows the images resulting from a topographic analysis of the actual collected images, wherein FIG. 9(*a*) is a slurry image and 9(*c*) is an image of water only. FIG. 9(*b*) and 9(*d*) show the topographic analysis (ridges and ravines only, for simplicity). The streak in FIG. 9(*a*) is very accurately characterized in 9(*c*), especially in comparison to the uniformity of 9(*d*).

The second subsystem of the preferred embodiment of the invention is the depth-profiling subsystem. As described above, this system also incorporates a CCD camera or other image recorder. The light used to illuminate the web to create the image can be incoherent light, but it is preferred to use coherent light. Thus, appropriate physical arrangement of the strobe light and camera described above for the first subsystem can result in incorporation of the second subsystem. Alternatively, the apparatus used for the second subsystem can be a separate apparatus. Similarly, the same or different processing and data storage units can be use for the two subsystems. The second system is described herein as a separate unit, with the understanding that partial or complete integration with the first system is preferred.

The depth-profiling system is designed to measure the depth profile of the wet end of the web in the cross direction downstream from the headbox. It can be placed so as to fully coordinate the images obtained with the images obtained by the first subsystem, that is, that the images for both systems be simultaneously obtained. Where this is not possible, relatively simple, well-known programs exist to ensure that the obtained data is correlated between the two systems.

In its preferred embodiment, the depth-profiling system uses structured lighting through the use of an infrared laser to produce images captured by a CCD camera. The images are recorded in real time and processed to characterize the depth characteristics of the web. Sequencing the images provides a continuous depth profile of the web. The laser is equipped with optics to produce a spread beam in a plane perpendicular to the machine direction of the web, parallel to the cross direction. The CCD camera is mounted at an angle to the laser to capture the light reflected from the web.

The actual equipment used may vary. An exemplary apparatus includes a Pulnix TM-9701 CCD, a Schneider 25-mm focal length C-mount lens, a Schneider screw-on mount linear polarizing filter, a Schneider infrared Pass filter, and a Lasiris 100-mW, 830-nm, IR diode laser with a 45° fanout line projector. The data processing and storage equipment includes a Datacube Maxvideo MV200 and a Motorola MVME167 image acquisition and processing system. The camera, lens, and processing system, it can be noted, are the same as for the stroboscopic system. The 830-nm laser light is invisible to the eye, but the silicon imaging system of the camera is highly sensitive to energy at this wavelength. The infrared pass filter filter excludes visible light. External light therefore does not interfere with the algorithm used to locate the laser line position.

Figure 10:
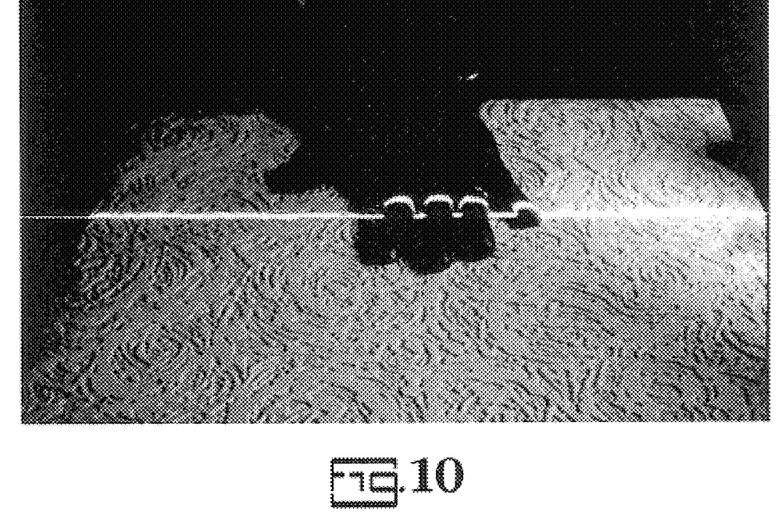
FIG. 10 is an illustrative image illustrating depth profiling according to the current invention.

The laser is set, for example, at a 45° to the web. With the camera at an angle 6 from the laser, the change in image height as seen by the camera is related to the actual depth changes by $$dy = \sin\theta\, dz$$

where dy is the change in the y coordinate relative to the camera, and dz is the change in depth. FIG. 10 illustrates this relationship in an image of a person's fingers placed in the fan beam. As the equation shows, depth sensitivity increases as the angle θ increases up to 90°. The larger the angle, however, the more probability there is that occlusion caused by surfaces not in the laser light plane will occur. Good results are obtained at θ=45°, where the sensitivity is about 70% of the maximum possible.

The laser illuminates the web, producing a reflection indicative of the depth profile of the web in the plane of the light. This image is captured by the camera, and the image data is transferred to the Datacube MV200 for processing. The MVME 167 CPU performs the primary processing to calculate the line position. While the image is being acquired, the MV200 applies a threshold function to the data and calculates the upper left and lower right coordinates of the bounding box that surrounds the laser line area above the threshold. Thereafter, only data within the bounding box is read by the CPU. This significantly reduces the amount of data that must be transferred to the CPU, and equally reduces local data storage capacity requirements. High storage capacity and high computational speed enable data acquisition and profiling computations in real time. Alternatively, for purposes such as research, the image data can be acquired in real time and processed later from memory.

After detecting the laser line, it is necessary to estimate the center of the line within each column of the image. The estimated centers or, more properly, the displacement thereof from a reference point, correspond to the depth profile of the web.

Two algorithms for this estimation were implemented with sample images obtained from a web. The first algorithm is referred to as the binary centroid algorithm. Within each column of the bounding box (columns referring to the appropriate pixels), the intensity values of the contained laser line are subjected to a threshold to produce a one-dimensional blob. The depth profile then of the object in each location is computed as the centroid of the obtained blob according to $$z = A^{-1} \Sigma_i r_i$$

where $r_i$ represents the coordinate (row position) of the pixels the intensity values of which fall above the threshold, and A is the total number of such pixels.

A more sophisticated and computationally complex algorithm can also be used. This is referred to as the weighted centroid algorithm. See F. W. DePiero and M. M. Trivedi, "3-D Computer Vision Using Structured Light: Design, Calibration and Implementation Issues," *Advances in Computers* 43, 1996, incorporated herein by reference. As above, this computation is repeated for each column of the bounding box that contains the laser line. The distinct characteristic of the weighted centroid algorithm is a smooth mapping function, $P(g_i)$, that is used to represent the likelihood that a pixel with intensity $g_i$ is a member of the laser line. This is in contrast to the binary centroid algorithm. In the binary centroid algorithm, through the utilization of the threshold, the decision whether or not a pixel is a member of the laser line is a crisp "true/false" decision. In the weighted centroid algorithm, the decision is fuzzy. A truncated error function (erf) is chosen for the smooth mapping function. The shape of the Gaussian, which is integrated to compute the values of $P(g_i)$, was chosen such that at a value 3σ below the mean were intensity values clearly belonging to the background. Then, the depth profile of the object in each column is calculated as $$z = [\Sigma_i P(g_i) r_i]/S$$

where $$S = \Sigma P(g_i).$$

The depth information estimated in this fashion, although computationally more intensive, is far more robust than the binary centroid algorithm. Thus, while the scope of the invention comprehends the use of either algorithm, and the choice of algorithm may be forced in practice by the computational capability of the equipment, it is preferred to use the weighted centroid algorithm for characterizing the depth of the web.

Figure 11A:
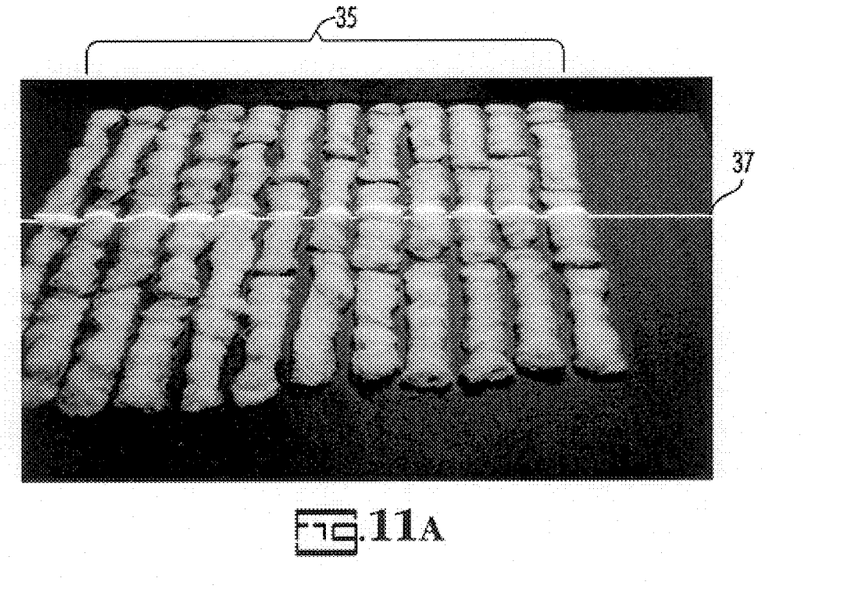
FIG. 11(a) shows a test set-up for depth profiling.
Figure 11B:
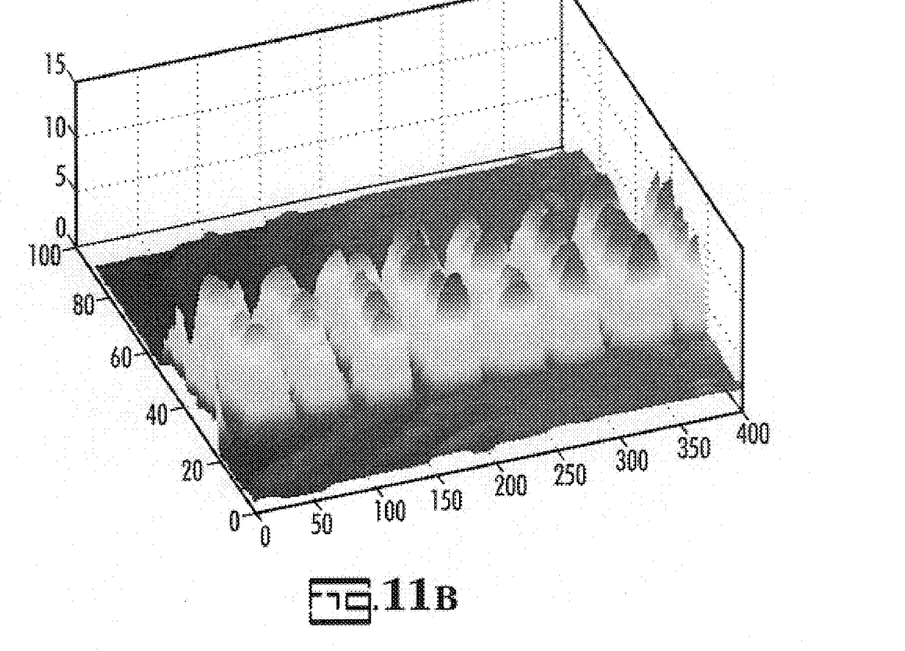
FIG. 11(b) shows depth profiling of the test set-up at a web speed of 100 ft/min.
Figure 11C:
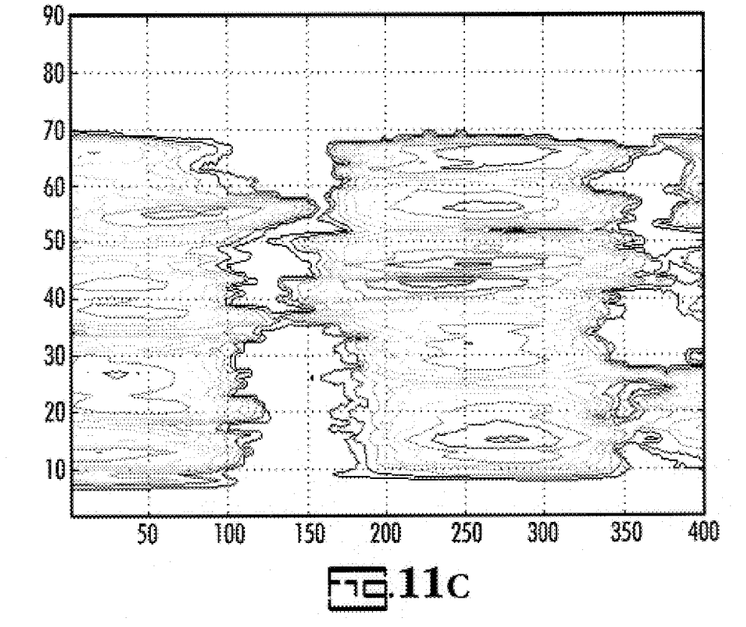
FIGS. 11(c)–11(e) show contour plots of the test set-up at varying web speeds.
Figure 11D:
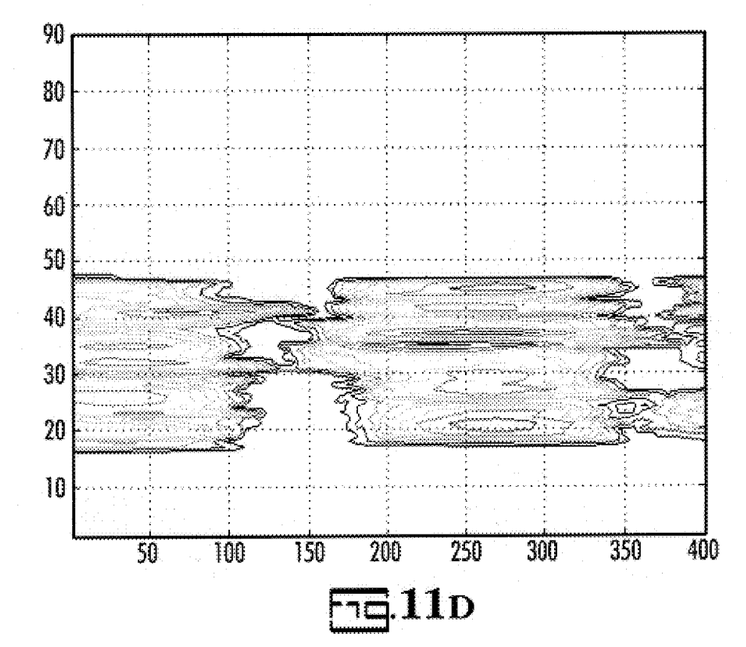
Figure 11E:
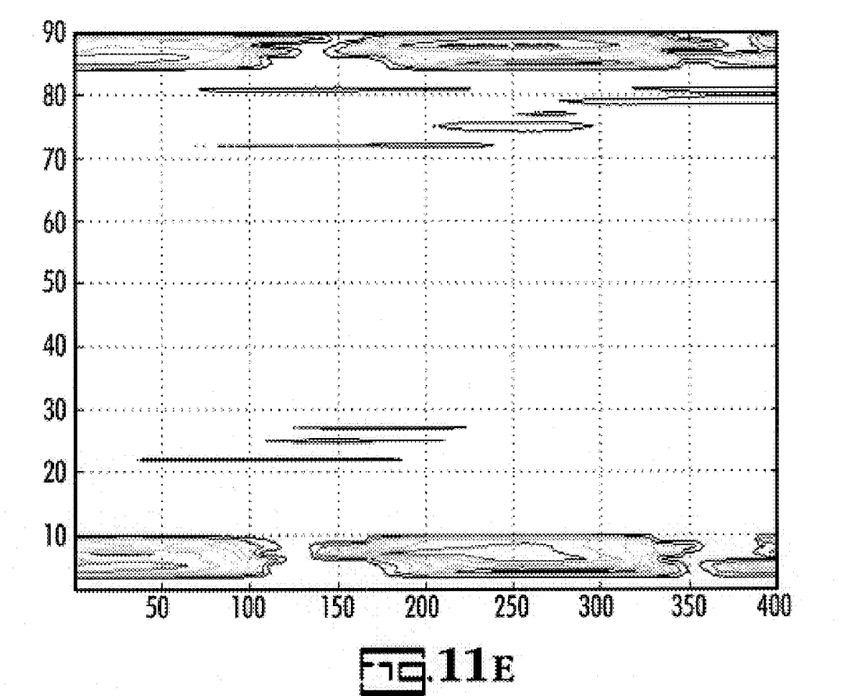

As a test of this system, a row of cotton balls 35 was glued to a surface of transported paper. The test set-up is shown in FIG. 11(a) indicating a laser line 37. This test scene was scanned by the depth profiling system at various web speeds. The depth profile of this test scene at a speed of 100 ft/min is shown in FIG. 11(b). Contour plots in two dimensions are shown at speeds of 50, 100, and 500 ft/min, respectively, in FIGS. 11(c), (d), and (e). It can be seen that the lengths of the observed rows are shortened as the number of samples in the machine direction decreases with increased web speed. The contour plots provide good detail regarding web nonuniformities as detected.

Figure 12A:
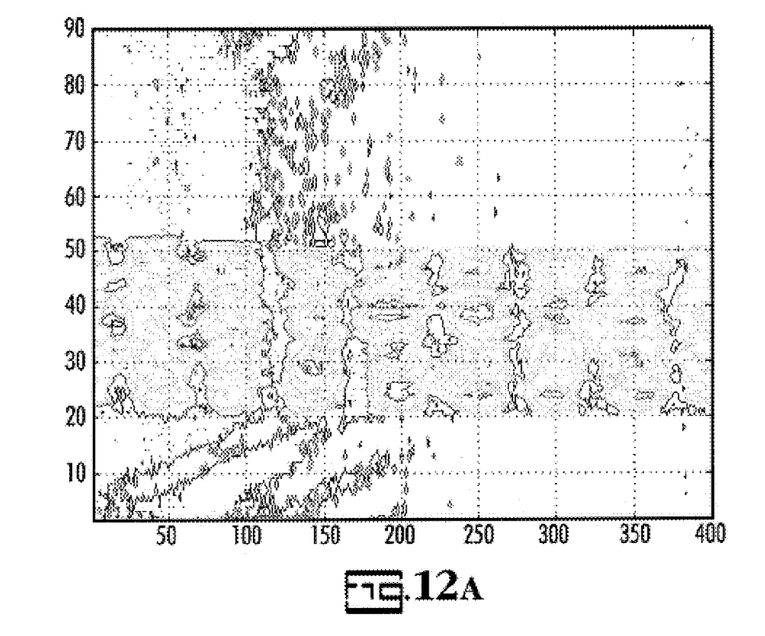
FIGS. 12(a) and 12(b) show plots illustrating a comparison between alternative depth profiling analysis algorithms.
Figure 12B:
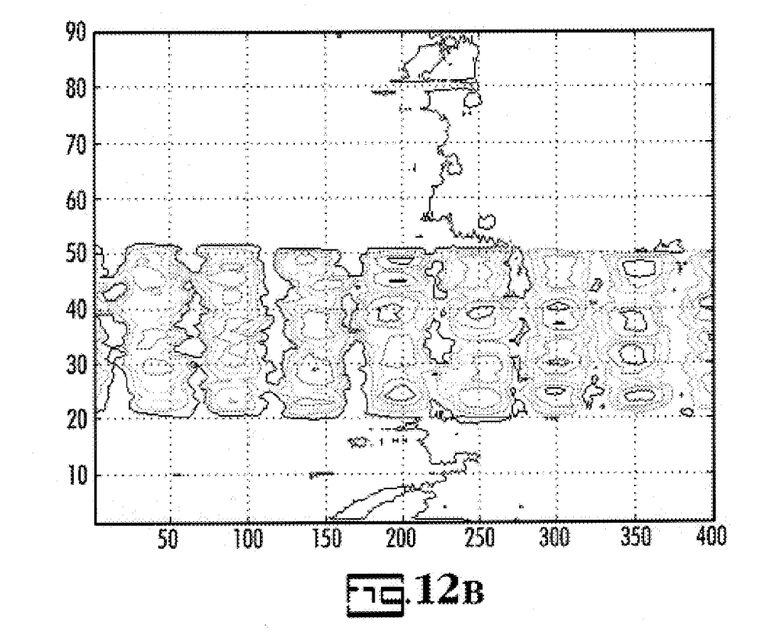

To compare the two types of algorithms described above, the test scene was processed through both algorithms. The results are shown in FIG. 12. The profile in FIG. 12(a), obtained from processing through the binary centroid algorithm, can be compared with the profile in FIG. 12(b) as processed via the weighted centroid algorithm. The profile in FIG. 12(a) is much more susceptible to noise, and the rows and peaks of the test scene are much better defined in FIG. 12(b) through use of the weighted centroid algorithm.

The data from the stroboscopic system and from the depth profiling system are easily registered with each other, such that a complete 4-D characterization is obtained for the web. The images encompass the entirety of the web as it is formed and processed, and can be made available in real time. The values can also be stored and subjected to complete review by utilizing data storage. The operator, or researcher, is thus provided with 2-D spatial information, intensity profiles including homogeneity values and topography, and depth profiling. The web is thus characterized in four dimensions, from which the characteristics and quality of the web can be assessed. The creation of a web in production can thus be controlled and understood. The data made available can also be used to quantify and characterize headbox flow dynamics and extrusion die dynamics.

The equipment specifically listed herein for the two systems is exemplary only. The cameras, filters, light sources, and other hardware may be varied depending on the application. Also, the computational equipment can vary. It is possible to utilize specially designed, dedicated processors to create a stand-alone integrated system, or the processors can consist of programmed, general purpose processors. These variations do not depart from the scope or intent of the invention, the scope of which is defined in the following claims.

What is claimed is:

1. A method of characterizing a web of sheet material in four dimensions, said method comprising:
   (a) illuminating said web with light energy at a point substantially adjacent to the initial formation of said web;
   (b) recording an input image of said web at said point during said illumination;
   (c) converting said image to a digital representation thereof;
   (d) processing said digital representation to determine the homogeneity of said web at said point, said determination of said homogeneity comprises:
      generating a multiscale wavelet representation of said digital representation to generate detail signals;
   (e) processing said digital representation to determine the topography of said web at said point;
   (f) processing said digital representation to determine the depth profile of said web at said point; and
   (g) providing respective output signals representative of said homogeneity, said topography, and said depth profile;
      whereby said web can be characterized at said point in four dimensions.

2. The method according to claim 1, wherein said determination of said homogeneity further comprises:
   computing for said detail signals the local roughness value R(m,n), where $$R(m,n) = \Sigma C^2(\epsilon, m, n)$$

where the summation is $\epsilon = 1$ to $\epsilon_u$, where $\epsilon_u$ is the upper limit for $\epsilon$, and C($\epsilon$, m, n) is the correlation sum computed within non-overlapping subregions of said detail signals; and
   computing for said detail signals the global image homogeneity value V, wherein $$V = Q^{-1} \Sigma_m \Sigma_n [R(m,n) - M]^2$$

where $$M = Q^{-1} \Sigma_m \Sigma_n R(m,n)$$

and Q is the total number of subregions into which said detail signals are divided.

3. The method according to claim 1, wherein said determination of said topography comprises:
   determining the cubic facet for each point on said input image and for the neighborhood of said point;
   deriving the gradient and Hessian for each of said cubic facets;
   determining from said gradient and said Hessian a topographic value set for each said point;
   determining from said topographic value set the topographic location of said point;
   combining the topographic locations of said points to provide a topography for said input image.

4. The method according to claim 1, wherein said determination of said depth profile comprises:
   recording as a depth image a single line of light reflected from said web;
   deriving from said depth image a boundary box image;
   dividing said boundary box image into columns;
   selecting an image object for each column;
   determining the depth profile z for each image object, wherein $$z = [\Sigma_i P(g_i) r_i]/S$$

where $g_i$ is the intensity of said image object for each said column; $P(g_i)$ is a smooth mapping function, and $$S = \Sigma P(g_i).$$

5. A method for determining the spatial dimension, intensity values, and topography of a web of sheet material, the method comprising
   (a) illuminating said web with light energy at a point substantially adjacent to the initial formation of said web;
   (b) recording an input image of said web at said point during said illumination;
   (c) converting said image to a digital representation thereof;
   (d) processing said digital representation to determine the homogeneity of said web at said point by
      generating a multiscale wavelet representation of said digital representation to generate detail signals;
      computing for said detail signals the local roughness value R(m,n), where $$R(m,n) = \Sigma C^2(\epsilon, m, n)$$

where the summation is $\epsilon = 1$ to $\epsilon_u$, where $\epsilon_u$ is the upper limit for $\epsilon$, and C($\epsilon$, m, n) is the correlation sum computed within non-overlapping subregions of said detail signals; and
      computing for said detail signals the global image homogeneity value V, wherein $$V = Q^{-1} \Sigma_m \Sigma_n [R(m,n) - M]^2$$

where $$M = Q^{-1} \Sigma_m \Sigma_n R(m,n)$$

and Q is the total number of subregions into which said detail signals are divided; and
   (e) processing said digital representation to determine the topography of said web at said point by
      determining the cubic facet for each point on said input image and for the neighborhood of said point;
      deriving the gradient and Hessian for each of said cubic facets;
      determining from said gradient and said Hessian a topographic value set for each said point;
      determining from said topographic value set the topographic location of said point;
      combining the topographic locations of said points to provide a topography for said input.

6. A method for determining the depth profile of a web of sheet material, the method comprising:

recording as a depth image a single line of light reflected from said web;

deriving from said depth image a boundary box image;

dividing said boundary box image into columns;

selecting an image object for each column;

determining the depth profile z for each image object, wherein $$z=[\Sigma_i P(g_i) r_i]/S$$

where $g_i$ is the intensity of said image object for each said column; $P(g_i)$ is a smooth mapping function, and $$S=\Sigma P(g_i).$$

7. Apparatus for analyzing the characteristics of a web comprising:

(a) a light source directed at said web capable of illuminating said web at a point adjacent the initial formation of said web;

(b) a detector for detecting and recording light transmitted by said web to form an image;

(c) a digitizer operatively connected to said detector for digitizing said image to produce a digital representation of said image;

(d) processor means for processing said digital representation to produce signals representative of the homogeneity, topography, and depth profile of said web, said processor means comprising means for generating a multiscale wavelet representation of said digital representation; and (e) output means operatively connected to said processor means to provide an indication of the four dimensional characteristics of said web.

8. Apparatus according to claim 7, wherein said light source comprises:

a stroboscopic lamp; and an infrared laser.

9. Apparatus according to claim 7, wherein said detector comprises a charge-coupled device responsive to both visible and infrared light energy.

10. A method of characterizing a web of sheet material in four dimensions, said method comprising:

(a) illuminating said web with light energy at a point substantially adjacent to the initial formation of said web;

(b) recording an input image of said web at said point during said illumination;

(c) converting said image to a digital representation thereof;

(d) processing said digital representation to determine the homogeneity of said web at said point, said determination of said homogeneity comprises:

generating a multiscale wavelet representation of said digital representation to generate detail signals;

computing for said detail signals the local roughness value R(m,n), where $$R(m,n)=\Sigma C^2(\epsilon, m, n)$$

where the summation is $\epsilon=1$ to $\epsilon_u$, where $\epsilon_u$ is the upper limit for $\epsilon$, and $C(\epsilon, m, n)$ is the correlation sum computed within non-overlapping subregions of said detail signals; and computing for said detail signals the global image homogeneity value V, wherein $$V=Q^{-1}\Sigma_m \Sigma_n [R(m,n)-M]^2$$

where $$M=Q^{-1}\Sigma_m \Sigma_n R(m,n)$$

and Q is the total number of subregions into which said detail signals are divided;

(e) processing said digital representation to determine the topography of said web at said point;

(f) processing said digital representation to determine the depth profile of said web at said point; and (g) providing respective output signals representative of said homogeneity, said topography, and said depth profile;

whereby said web can be characterized at said point in four dimensions.

11. A method of characterizing a web of sheet material in four dimensions, said method comprising:

(a) illuminating said web with light energy at a point substantially adjacent to the initial formation of said web;

(b) recording an input image of said web at said point during said illumination;

(c) converting said image to a digital representation thereof;

(d) processing said digital representation to determine the homogeneity of said web at said point;

(e) processing said digital representation to determine the topography of said web at said point;

(f) processing said digital representation to determine the depth profile of said web at said point, wherein said determination of said depth profile comprises:

recording as a depth image a single line of light reflected from said web;

deriving from said depth image a boundary box image;

dividing said boundary box image into columns;

selecting an image object for each column;

determining the depth profile z for each image object, wherein $$z=[\Sigma_i P(g_i) r_i]/S$$

where $g_i$ is the intensity of said image object for each said column; $P(g_i)$ is a smooth mapping function, and $$S=\Sigma P(g_i); \text{ and}$$

(g) providing respective output signals representative of said homogeneity, said topography, and said depth profile;

whereby said web can be characterized at said point in four dimensions.

* * * * *